United States Patent
Wallén et al.

[19]

[11] Patent Number: 6,058,786
[45] Date of Patent: May 9, 2000

[54] DEVICE FOR MEASURING A GAS FLOW

[75] Inventors: Lars Wallén, Sundbyberg; Carl-Erik Arvidsson, Solna, both of Sweden

[73] Assignee: Siemens Elema AB, Solna, Sweden

[21] Appl. No.: 09/274,862

[22] Filed: Mar. 23, 1999

[30] Foreign Application Priority Data

Mar. 25, 1998 [SE] Sweden ................................. 9801007

[51] Int. Cl.⁷ ..................................................... G01F 1/66
[52] U.S. Cl. ...................................................... 73/861.28
[58] Field of Search .......................... 73/861.28, 861.25, 73/861.26, 861.27, 861.29, 861.31; 128/719, 716, 729

[56] References Cited

U.S. PATENT DOCUMENTS

| | | | |
|---|---|---|---|
| 3,869,915 | 3/1975 | Baumoel ................................ | 73/861.28 |
| 4,321,835 | 3/1982 | Martin . | |
| 5,419,326 | 5/1995 | Harnoncourt . | |
| 5,645,071 | 7/1997 | Harnoncourt et al. ................ | 73/861.28 |

FOREIGN PATENT DOCUMENTS

| | | |
|---|---|---|
| 0 260 335 | 3/1988 | European Pat. Off. . |
| 0 677 722 | 10/1995 | European Pat. Off. . |
| 0 874 238 | 3/1998 | European Pat. Off. . |
| 28 12 464 | 9/1978 | Germany . |
| 94 10 661 | 11/1994 | Germany . |
| 44 30 223 | 3/1995 | Germany . |
| WO 94/28790 | 12/1994 | WIPO . |
| WO 95/11426 | 4/1995 | WIPO . |

OTHER PUBLICATIONS

"Impedance–Matched Metallurgically Sealed Transducers," Lynnworth et al., IEEE Trans. on Sonics and Ultrasonics, vol. SU–31, No. 2, Mar. 1984, pp. 101–104.

*Primary Examiner*—William Oen
*Attorney, Agent, or Firm*—Hill Simpson

[57] ABSTRACT

A device for measuring a gas flow, has a measurement chamber and an ultrasonic transceiver unit which can be attached to the measurement (chamber over openings of the measurement chamber and which is provided with transmit and receive heads. The heads are directed against the openings of the measurement chamber, membranes being arranged between the measurement chamber and the transmit and receive heads which are permeable to ultrasound waves but largely impermeable to moisture and bacteria. In order to feed maximum acoustical energy to the ultrasonic transceiver unit while keeping moisture and bacteria away from the unit, the membranes are replaceably arranged close to the transmit and receive heads.

4 Claims, 2 Drawing Sheets

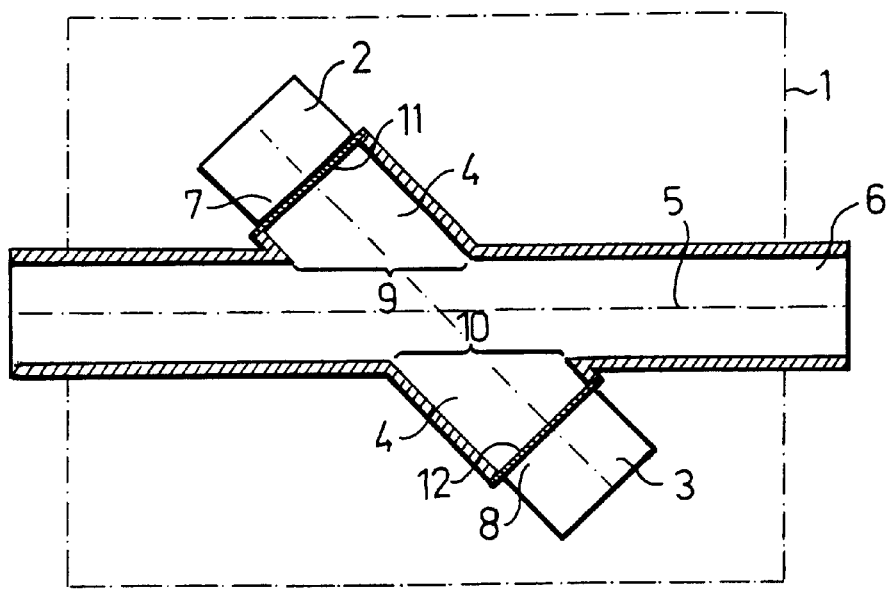
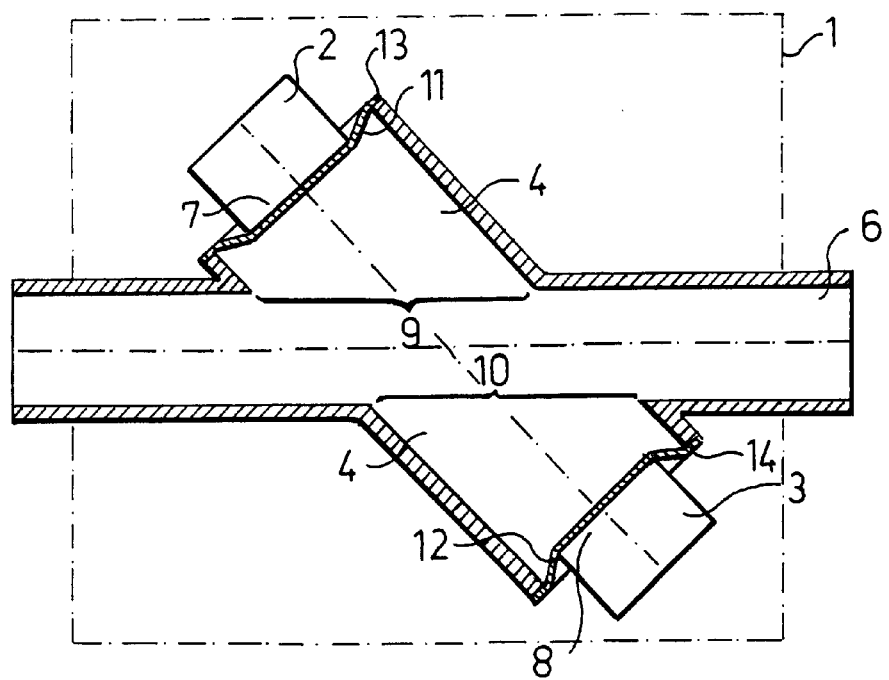

DEVICE FOR MEASURING A GAS FLOW

BACKGROUND OF THE INVENTION

1. Field of the Invention

The invention relates to a device for measuring a gas flow, of the type having a measurement chamber and an ultrasonic transceiver unit which can be attached to the measurement chamber over the openings thereof and which is provided with transmit and receive heads which are oriented against the openings of the measurement chamber, with membranes being arranged between the measurement chamber and the transmit and receive heads which are permeable to ultrasound waves, but largely impermeable to moisture and bacteria.

2. Description of the Prior Art

German PS4 222 286 describes an ultrasonic flow meter of the above type in which the transmitter and the receiver are arranged at a distance from each other along a measuring tube. The measuring length extends obliquely to the axis of a tubular measurement chamber through which the medium flows whose flow rate is to be determined. This flow meter is known as a spirometer for determining the lung capacity of the patient. In order to maintain hygiene, a sterile insertion tube is inserted into the measurement chamber with each new patient. The sterile tube is provided with measurement windows which are fitted so that they are situated over the openings. Membranes which are permeable to ultrasound signals but impermeable to moisture and bacteria are arranged in the measurement windows, so that the ultrasound signals along the measuring tube can pass through the sterile insertion tube. It is therefore unnecessary for the hospital personnel to autoclave the flow meter after every use, which is advantageous since the ultrasonic transceiver unit, in particular, are sensitive parts in the flow meter. In connection with the known ultrasonic flow meer, the membranes, which are arranged at a distance from the ultrasonic transmit and receive heads, can be foam rubber, in one example, and a Mylar® film, in another. In connection with the first example, in order to be able to reach the transmit or receive unit, the ultrasound signals must first pass through the relatively thick foam rubber membrane, and then a relatively large air gap. This transition from a relatively thick membrane to a relatively large air gap can lead to a high acoustical impedance, i.e. to a high sound wave reflection. This can lead to relatively large acoustical losses, so that an unacceptably low sound signal reaches the transmit or receive heads. A relatively low acoustical impedance is associated with the use of a Mylar® film, due to its extreme thinness, so that a receivable sound signal can reach the aforementioned heads. The disadvantage of Mylar® films which are attached as described is that they are so thin and sensitive that they cannot always withstand the mechanical stress they are exposed to when a pressure excess arises in the measurement chamber, which can cause the films to easily rip.

SUMMARY OF THE INVENTION

It is an object of the present invention to provide a device of the type initially described wherein maximum acoustical energy is fed to the ultrasonic transceiver unit, while moisture and germs are kept away from the unit.

This object is inventively achieved in a device for measuring a gas flow the membranes are removably arranged close to the transmit and receive heads. Since the membranes are removable, they can be removed after an examination and replaced by new membranes in connection with a new patient. As an alternative, the membranes can potentially be cleaned and reused. Since the membranes are arranged close to the transmit and receive heads, the acoustical impedance is effectively lowered, and more acoustical energy is fed to these heads. Due to the placement of the membranes, very thin metal or polymer membranes can be used, for example, since they are no longer exposed to a mechanical stress in this position. A thicker membrane, made of foam rubber, for example, can now be used with nearly an equally good acoustical energy feed to the transmit and receive heads. The advantage of a thick membrane is its good durability.

The article "Impedance-Matched Metallurgically Sealed Transducers" (*IEEE Transactions on Sonics and Ultrasonics*, Vol. SU-31, No. 2, March 1984:101–104) teaches a robust ultrasonic sensor whose head is provided with a relatively thick membrane, which is connected to the sensor and which is permeable to ultrasound waves, but not to moisture and bacteria. In front of the membrane, a thin plastic film is attached which is provided exclusively to reduce the acoustical impedance, which is otherwise relatively high if a metal membrane as described is used. It is not stated in the article that the thin plastic film eliminates the possibility of moisture and bacteria reaching the metal membrane. Thus, despite the metal membrane and the plastic film, it is necessary when using this sensor in connection with an ultrasonic flow meter to autoclave this sensor prior to each new patient, since moisture and bacteria may be present on the metal membrane. Regular auto claving of the sensor results in a shortened lifetime.

In an embodiment of the inventive device, each transmit and receive head presses against the respective membrane. In such an embodiment, the membranes are fastened in the measurement chamber removably, for example. If the heads are pressed against the respective membranes, nearly all the air between the membrane and the head is pressed to the side, so that the heads become situated close to the respective membrane, thereby enabling a further reduction of the acoustical impedance.

In another embodiment of the inventive device, it is proposed that the membrane is attached to the transmit and receive head. The heads of the transmitter and of the receiver can thus be provided with membranes before being attached to the measurement chamber. Subsequent to the examination, the transmitter and receiver are detached from the measurement chamber, the membranes are replaced and the transmitter and receiver are used in connection with a new patient.

In another embodiment of the inventive device, each transmit and receive head is connected to the membrane by means of an adhesive, at least over a part of the head surface. The membrane is appropriately provided with an adhesive layer. The adhesive layer is removed from the head in the replacement of the membrane. Because the membrane has a mechanical connection to the head in this type of embodiment, the acoustical impedance is again lowered. There is mechanical stability of the membrane here as well.

DESCRIPTION OF THE DRAWINGS

FIG. 1 shows the basic components of a first embodiment of an inventive measuring device, in a longitudinal section.

FIG. 2 shows the basic components of a second embodiment of inventive measuring device, in a longitudinal section.

DESCRIPTION OF THE PREFERRED EMBODIMENTS

Figure 3:
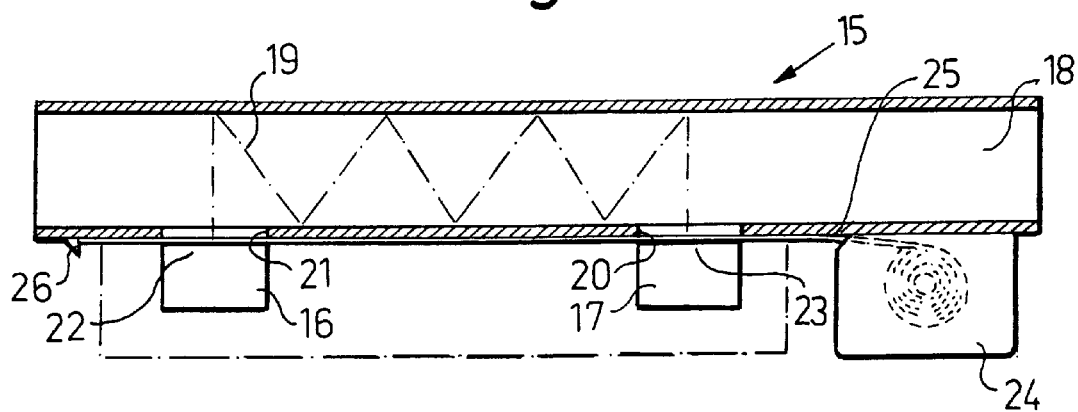
FIG. 3 shows the basic components of a third embodiment of an inventive measuring device, in a longitudinal section.

FIG. 1 schematically depicts an ultrasonic flow meter 1 wherein an ultrasonic transmitter 2 and an ultrasonic receiver 3 is and arranged along a channel 4, which serves as a measuring length, at a distance from one another. The channel 4 extends obliquely to the axis 5 of a tubular measurement chamber 6 through which the medium flows whose flow rate is to be determined. The flow meter is what is known as a spirometer for determining the lung capacity of the patient. The ultrasonic transmitter 2 and the receiver 3 are respectively provided with transmit and receive heads 7,8, which are directed toward respective openings 9, 10 in the measurement chamber 6 through which the measuring length extends. This general type of ultrasonic flow meter 1 is demonstrated and described in PCT Application WO 94/28790. Membranes 11, 12 are provided in the inventive ultrasonic flow meter 1 which are permeable to ultrasound waves but largely impermeable to moisture and bacteria and which are arranged close to the transmit and receive heads 7, 8. In this exemplary embodiment, the inner diameter of the channel 4 is approximately as large as the outer diameter of the transmit and receive heads 7,8. In this type of embodiment it is advantageous to attach the membranes 11, 12 directly to the transmit and receive heads 7, 8, respectively, with an adhesive, for example. The application of the metal or polymer membranes 11, 12 close to the respective transmit and receive head 7,8 results in a relatively low acoustical impedance, enabling a relatively large amount of acoustical energy to be supplied. Given this type of application, relatively thick membranes can be attached without a notable reduction of the acoustical energy reaching the respective heads 7, 8. A very small acoustical impedance is obtained if a thin membrane is used. Since the membranes 11, 12 are connected to the respective heads 7,8 via an adhesive in the exemplary embodiment, the membranes 11, 12 are brought into mechanical contact with the heads 7, 8, achieving a further reduction of the acoustical impedance. Since the membranes 11, 12 are replaceable, they are removed after an examination, and new membranes 11, 12 are applied prior to each new patient. As an alternative, the membranes 11, 12 can be autoclaved and reused.

FIG. 2 shows an ultrasonic flow meter 1, which differs from the ultrasonic flow meter 1 described in connection with FIG. 1 in that the inner diameter of the channel 4 is greater than the outer diameter of the respective transmit and receive heads 7, 8. Another difference is that the membranes 11, 12 are removably attached to the respective open ends 13, 14 of the channel 4. By pressing the respective heads 7, 8 of the transmitter 2 and the receiver 3 against the respective membranes 11, 12, almost all the air between the membranes 11, 12 and the heads 7, 8 is expelled, allowing the heads 7, 8 to be situated close against the membranes 11,12. In this exemplary embodiment, the membranes 11,12 need not be provided with an adhesive. In connection with the embodiment described in FIG. 2, the ultrasonic transmitter 2, the ultrasonic receiver 3 and the membranes 11, 12 can be removed after each examination, and new membranes can be applied to the respective heads 7, 8 prior to each patient. The transmitter and receiver are subsequently pressed against the respective membranes 11, 12 again, as described, and are locked in this position.

FIG. 3 depicts another schematically illustrated ultrasonic flow meter 15. In connection with this flow meter, the transmitter 17 and the receiver 18 are arranged on the same side of the elongated measurement chamber 18. The transmitter 16 can emit an acoustical signal, referenced 19, which is transmitted, via a number of reflections at the walls of the measurement chamber 18, through a gas mixture that flows through the measurement chamber 18, in order to subsequently strike the receiver, which accepts the transmitted acoustical signal. This general type of ultrasonic flow meter 15 is detailed in European Application 0 874 238. The diameter of those openings 20, 21 which are arranged at the measurement chamber and which are provided for the transmitter 16 and the receiver 17 is inventively approximately equally as large as the outer diameter of the respective heads 22, 23 of the transmitter 16 and the receiver 17. In this exemplary embodiment, a retainer 24 is arranged at the measurement chamber 18, containing a rolled stock of ribbon-shaped membrane 25. Prior to an examination, the ribbon-shaped membrane 25 is rolled far enough out of the retainer so that it covers the two openings 20, 21 of the measurement chamber 18. The membrane 25 can be provided with an adhesive at least on the side which comes to rest against the outer wall of the measurement chamber 26, in order to be able to apply the membrane rapidly and easily. The transmitter 16 and the receiver 17 are subsequently attached against the membrane 25 at the respective openings 21, 22. The membrane 25 can also be provided with an adhesive on the side directed opposite the measurement chamber 18. This is preferred and results in a very good contact between the heads 22, 23 and the membrane 25. The outer wall of the measurement chamber 18 is provided with a tear part 26 for the membrane 22. Subsequent to an examination, the transmitter 16 and the receiver are removed. The membrane 25 is detached from the outer wall of the measurement chamber 18. Subsequently, another length of membrane 25 is pulled out of the retainer 25 prior to the next examination, until the membrane 2 covers the openings 21, 22, the membrane 25 which was used in the preceding measurement being torn off with the aid of the tear part 26. The transmitter 16 and the receiver 17 are subsequently applied against the membrane 25 again.

Figure 4:
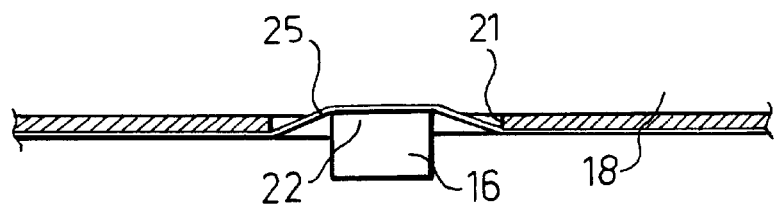
FIG. 4 shows the structure of a part of a measuring device according to FIG. 3.

FIG. 4 illustrates that the openings 20, 21 can be larger than the outer diameter of the respective head 22,23 of the transmitter 16 and of the receiver 17. In this exemplary embodiment, the transmitter 16 or the receiver 17 can be pressed against the membrane in order to reduce an air gap between said parts to a minimum, as described in connection with FIG. 2. In connection with this example, the part of the membrane 25 which faces the transmitter 26 or the receiver 17 need not necessarily be provided with an adhesive. The FIG. 4 depicts the opening 21 with the transmitter 16 only.

Figure 5:
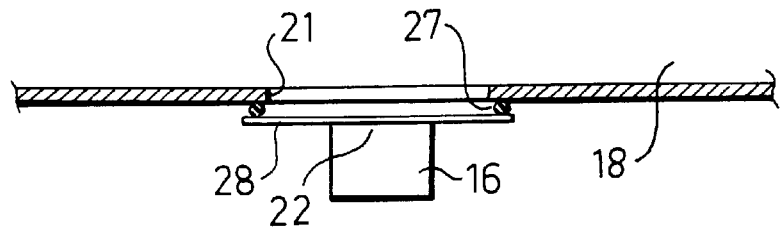
FIG. 5 shows the construction of the same part of the measuring device as in FIG. 4, but in another embodiment.

FIG. 5 illustrates that a sealing ring can be attached between the outer wall of the measurement chamber 18 and the membrane 28. In this type exemplary embodiment, it is advantageous for each opening 20, 21 of the measurement chamber 18 to be respectively provided with a membrane 28. The sealing ring 27 produces a good seal between the interior of the measurement chamber 18 3nd the atmosphere. FIG. 5 depicts the opening 21 with the transmitter 16 only. The opening 20 and the receiver 17 preferably have the same shape.

Although the present invention has been described with reference to a specific embodiment, those of skill in the art will recognize that changes may be made thereto without departing from the scope and spirit of the invention as set forth in the appended claims.

We claim as our invention:

1. A device for measuring a gas flow comprising:

a measurement chamber through which a gas flows, said measurement chamber having a first opening and a second opening therein;

an ultrasound transceiver having a transmit head communicating with an interior of said measurement chamber through said first opening and a reception head communicating with an interior of said measurement chamber through said second opening;

a first membrane removably dispose over said first opening substantially adjacent to said transmit head and a second membrane removably disposed over said second opening substantially adjacent to said reception head, each of said first and second membranes being permeable to ultrasound and impermeable to moisture and bacteria.

2. A device as claimed in claim 1 wherein said transmit head is pressed against said first membrane and wherein said reception head is pressed against said second membrane.

3. A device as claimed in claim 1 wherein said first membrane is attached to said transmit head and wherein said second membrane is attached to said receive head.

4. A device as claimed in claim 1 wherein said transmit head is connected to said first membrane by an adhesive at least over a part of a head surface of said transmit head, and wherein said reception head is connected to said second membrane by an adhesive at least over a part of a head surface of said reception head.

* * * * *